US009792682B2

(12) United States Patent
Gluncic et al.

(10) Patent No.: US 9,792,682 B2
(45) Date of Patent: Oct. 17, 2017

(54) TRAINING SYSTEM FOR DETECTION AND CLASSIFICATION OF ARTIFICIAL OBJECTS IN X-RAY IMAGES

(71) Applicant: RaPID Platforms, LLC, Chicago, IL (US)

(72) Inventors: Vicko Gluncic, Chicago, IL (US); Gady Agam, Naperville, IL (US); Mario Moric, Lincolnwood, IL (US)

(73) Assignee: RaPID Platforms LLC, Chicago, IL (US)

( * ) Notice: Subject to any disclaimer, the term of this patent is extended or adjusted under 35 U.S.C. 154(b) by 0 days.

(21) Appl. No.: 14/846,997

(22) Filed: Sep. 7, 2015

(65) Prior Publication Data

US 2017/0069081 A1     Mar. 9, 2017

(51) Int. Cl.
| | |
|---|---|
| *G06K 9/00* | (2006.01) |
| *G06T 7/00* | (2017.01) |
| *G06F 19/00* | (2011.01) |
| *A61B 8/00* | (2006.01) |
| *A61B 6/02* | (2006.01) |
| *A61B 6/03* | (2006.01) |
| *A61B 5/055* | (2006.01) |

(52) U.S. Cl.
CPC ............ *G06T 7/0012* (2013.01); *A61B 5/055* (2013.01); *A61B 6/02* (2013.01); *A61B 6/037* (2013.01); *A61B 8/00* (2013.01); *G06F 19/321* (2013.01); *G06T 2207/10116* (2013.01); *G06T 2207/20004* (2013.01); *G06T 2207/20081* (2013.01); *G06T 2207/30052* (2013.01)

(58) Field of Classification Search
CPC ......... G06T 2207/10116; G06T 7/0012; G06T 2207/30004; G06T 5/40; G06T 2207/30068
USPC ......................................................... 382/132
See application file for complete search history.

(56) References Cited

U.S. PATENT DOCUMENTS

| | | | |
|---|---|---|---|
| 6,208,884 B1* | 3/2001 | Kumar ............... | A61B 5/04005 324/207.21 |
| 2002/0077537 A1* | 6/2002 | Avrin ................. | A61B 5/04005 600/409 |
| 2003/0216632 A1* | 11/2003 | McClure .................. | A61B 5/05 600/409 |
| 2015/0141806 A1* | 5/2015 | Smith .................... | A61B 5/064 600/424 |

OTHER PUBLICATIONS

Bhuvaneswar et al., "Embedded Based on Medical Technology", Jul. 31, 2015, ICIEMS, pp. 236-243, retrieved from Internet on Nov. 10, 2016 from <http://edlib.net/2015/iciems/978-81-929742-7-9.pdf>.*
Theodore C. Marentis et al., "Surgical Retained Foreign Object (RFO) Prevention by Computer Aided Detection (CAD)" pp. 236-243, 2014, retrieved from Internet on Nov. 10, 2016 from <https://www.ncbi.nlm.nih.gov/pubmed/25735276>.*

* cited by examiner

*Primary Examiner* — Gregory F Cunningham
(74) *Attorney, Agent, or Firm* — Kevin R. Erdman; Brannon Sowers & Cracraft PC

(57) ABSTRACT

The present invention involves a software based system and method which provides a series of training images with or without retained surgical items in scans that are used to train human physicians to detect such items at varying levels of difficulty.

19 Claims, 8 Drawing Sheets

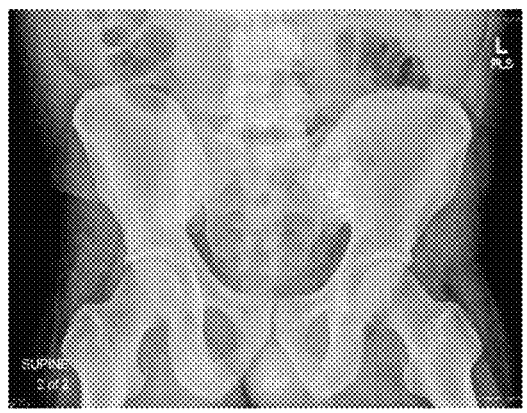 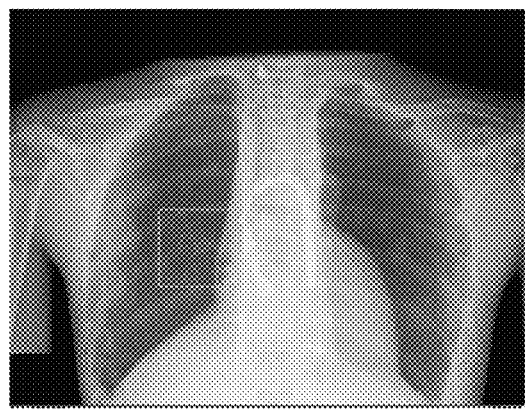
Figure 4A            Figure 4B

TRAINING SYSTEM FOR DETECTION AND CLASSIFICATION OF ARTIFICIAL OBJECTS IN X-RAY IMAGES

BACKGROUND OF THE INVENTION

Field of the Invention

The invention relates to medical pattern recognition systems and methods. More specifically, the field of the invention is that of training software for detection of retained foreign objects.

Description of the Related Art

Techniques are known for the identification of implanted medical devices ("IMDs") and retained foreign objects ("RFOs") in medical images.

Approximately 25 million patients in the United States have or have had an implanted medical device ("IMD"). Driven by a rapidly increasing aged population and supported by new technologies, the demand for IMDs and their further proliferation can only be expected to increase.

An IMD is a medical device that is partly or totally surgically inserted into the human body or a natural orifice and is expected to remain implanted for an extended period or may be permanent. IMDs can further be classified as either active, those that use electricity, or passive, those that do not use electricity. In the US, medical devices are regulated by the FDA and classified into three classes, on basis of risk and the level of regulatory control that is necessary to assure the safety and effectiveness: class I, class II, and class III. Class III devices include devices that generally affect the functioning of vital organs and/or life support systems with very high health risk if the device were to malfunction.

Identification of an IMD during patient admission, and especially in emergencies, is crucial for the safe and efficient management of that patient. Concerns with the accurate and timely identification of IMDs are an emerging safety issue. Of particular concern is the commonly encountered situation where medical records are not available and/or the patient is unable to provide the appropriate information/documentation regarding the IMD he has. Most commonly IMDs are initially reported by patients or noted on admission and/or emergency xrays ("XRs"), magnetic resonance images ("MRI"), ultrasound or computerized tomography ("CT") images, necessitating, often ineffective, attempts to gather more information regarding the device in question. This usually involves contacting the patient's family, primary care providers or health care institutions previously visited by the patient. Even when such attempts are successful, available information about the patient's device is often incomplete, unreliable and delayed. On the other hand, the large variety, rapidly increasing number approved by FDA, and difficult projections/orientations of IMDs in medical images (XR, CT, or MRI) make their identification very difficult for radiology specialists. Possible consequences include: delayed appropriate diagnostic imaging and care, medical complications arising from device incompatibility with imaging or therapeutic modalities, and suboptimal care due to inappropriate avoidance of treatment and diagnostic procedures that are erroneously considered contraindicated.

Software applications facilitate initial assessment/identification, expedite the management, and improve the healthcare and safety of patients with IMDs, including those with symptoms of IMD malfunction. They also facilitate implementation of recent FDA requirements for post-market device surveillance.

Physicians are increasingly encountering patients with IMDs. Identification of an IMD, during an emergent admission in particular, is critical for safe and efficient patient management. In 2007, FDA issued a report indicating an increase in adverse events linked to medical devices, including 2,830 deaths, 116,086 injuries, and 96,485 device malfunctions. Class III active IMDs were cited in a relatively high number of fatality reports within the FDA report.

Ultra-low-power radio-frequency (RF) technology has greatly facilitated the development of IMDs. The ability to wirelessly transmit the patient's and IMD's data enables a clinician to obtain useful diagnostic information and reprogram therapeutic settings. Furthermore, radio-frequency identification (RFID) technology uses radio waves to transfer data from an electronic tag to identify and track the tagged device. However, the rapidly increasing number of IMDs and their manufacturers, absence of the standardized tools/methods capable of RF sensing, identifying, and reprogramming IMDs, radio interference problems, ethical/security issues, and the fact that many IMDs do not have RF capabilities make this technology less convenient for rapid identification. This disadvantage is particularly obvious in medical emergencies and emergency room settings.

Medical errors involving IMDs, especially those arising from their incompatibility with treatment or diagnostic procedures, are an emerging patient safety issue. Procedures incompatible with patient's devices have been performed, leading to device malfunction and other complications. Examples of such complications include: patients undergoing Magnetic Resonance Imaging (MRI) in the presence of implanted ferromagnetic devices possibly causing migration, interference with the function of implanted devices because of strong magnetic fields (MR) and disrupting electrical forces (certain types of CT or surgical electrocautery). This includes setting changes of active (none turned off) cardiac pacemakers and defibrillators and/or defibrillation shocks during surgical procedures caused by electrocautery scalpels. In another example, percutaneous catheters and ports have been damaged by exceeding their pressure ratings during therapeutic infusions, necessitating subsequent surgical interventions/exchange or repair. Furthermore, several IMDs are compatible with MRI and CT imaging but/and/or requires reprogramming after the completion of the MRI which has been frequently missed. These effects on the IMD are not always evident or immediately observed (such as unintended re-programming, e.g., ventriculo-peritoneal shunts' valves) and can not only lead to delays but also to serious and possibly disastrous complications. Conversely, there are patients that do not receive optimal treatment and diagnostic procedures, even though their devices are compatible with such treatments. For example, several pacemakers currently on the market are compatible with MRI. In these cases, disclosure software identifies these specific models as being compatible with MRI, providing the treating physicians an option to have their patient undergo a medically-indicated MRI scan safely.

Retained foreign objects (RFOs) in patients due to oversights during surgery, objects including needles and surgical instruments and/or materials, continues to be a significant problem with an incidence of between 0.3 and 1.0 per 1,000 surgeries. This has resulted in a significant increase in patient care costs and consecutive legal expenses.

Intra-operative or early post-operative identification of RFOs is critical for safe and efficient management of surgical patients. Current recommendations for prevention of RFOs in the operating room ("OR") include methodical wound exploration before closing, usage of standardized practices for surgical items accounting, usage of items with radioopaque markers within the operative site, and mandatory operative field X-rays before wound closure when a item count discrepancy occurs. In addition, radiographic screening is recommended at the end of an emergent surgical procedure, unexpected change in the procedure, and for patients with a high body mass index. Some institutions also conduct routine postoperative screening radiographs for the prevention of RFOs. Therefore portable X-ray radiological protocols have become crucial for timely RFO detection. However, they have relatively low efficacy and require significant time for completion and for evaluation. The underlying problems of their use are the relatively low sensitivity and specificity of the human eye in the identification of relatively small objects in a large X-ray field and the fact that radiologists and surgeons do not routinely undertake formal training in the recognition of RFOs.

Technological aids to assist the OR team in the detection and prevention of retained sponges, gauze towels, and laparotomy pads include radio-frequency detectable sponge systems and bar-coded sponge systems. These aids are intended to augment the standardized manual count practices, and to not replace them.

Operative field X-ray is mandatory when there is a counting discrepancy of surgical instruments or materials at the end of the procedure. According to the 2006 Patient Care Memorandum of the Department of Veterans Affairs (Boston Healthcare System, VA, USA), surgical instruments and/or materials must be counted, except for procedures that are routinely concluded with a radiograph (for example, an orthopedic case to assure proper alignment of a bone or implant). In these cases, a radiograph is mandatory if an instrument count is not performed, and the evaluation of the radiograph must be performed before the patient is transferred from the OR to determine whether any instruments have been retained. When a radiograph is requested to locate a missing item, the type of foreign object that is missing, OR number, and telephone number must be specified in the request to the radiologist. Radiographic screening is also recommended/mandatory at the end of emergent surgical procedures, unexpected changes in procedures, or in patients with high BMI (e.g. >=20). Some institutions use postoperative screening radiographs routinely. In all of these cases, the completion of the surgical case may be delayed until radiologic evaluation is received. Assuming the patient is stable, current recommendations are that in the event of an incorrect count, a X-ray of the operative field should be made available to a radiologist within 20 minutes and their evaluation/confirmation of the results of the x-ray should be provided back to the OR within another 20 minutes. This process frequently takes significantly more time than 40 minutes.

Portable X-ray is also a method of choice for determination of the relative position/location of a RFO. This is particularly important if the specific tissue layer or surgical incision/wound is already closed and additional instruments are present in the X-ray image.

While stainless steel instruments are likely to be detected successfully on radiograph screening, radiographs are less sensitive in detecting sponges and needles. Sponges may be difficult to detect because they may become twisted or folded, distorting visualization of the marker. Needles may also be difficult to visualize due to their size. The value of intraoperative and/or post-operative X-ray images for RFO identification has been controversial and very few studies have been undertaken to evaluate their effectiveness. A recent study evaluating portable X-rays for identification of retained suture needles in ophthalmologic surgical cases showed that the overall sensitivity and specificity of the physicians' review of radiographs with suspected retained needles was 54% and 77%, respectively. This is particularly worrisome considering that in this particular case the size of the surgical field was small, the area of interest well-defined, while the participants in the study have known that they were looking for the needles which should have greatly facilitated RFOs/needle detection. In the most studies when radiographs were falsely negative for RFO detection; poor-quality radiographs, multiple foreign objects in the field, and failure to communicate the purpose of the radiograph to the interpreting radiologist were cited as contributing factors. Although it is mandatory that such intra-operative radiographs be reviewed by a radiologist(s) and/or surgeon(s), it is not routine for those individual to have undertaken specific/formal training in the radiographic identification/recognition of these objects. Furthermore, the general consensus throughout the literature is that the most effective means of evaluating the presence of a RFO is through the use of CT scanning which—in most of the cases—is not possible in the OR.

Even when attuned to the problem of RFOs, both physicians and detection software suffer from the lack of samples with which to test. Physicians, and particularly radiologists, are infrequently provided a scan image having an RFO so that they have no opportunity to develop their skills in this area. Detection software, similarly, is difficult to test and develop because the lack of such images.

SUMMARY OF THE INVENTION

The present invention is embodied, in one aspect, by a RFO image system and method which allows for the synthesis of realistic RFO images which may be used by physicians and/or detection software to develop RFO recognition skills. In another aspect, the invention is embodied by a physician training system configured to provide physicians with experience in recognizing scans of RFOs. In each of these illustrative embodiments, scan images of both actual and synthetic RFOs are used without differentiation, and the resulting systems and methods are achieved with the assistance of the additional RFO images that are available to provide a variety, and a larger number of, such scan images.

BRIEF DESCRIPTION OF THE DRAWINGS

The above mentioned and other features and objects of this invention, and the manner of attaining them, will become more apparent and the invention itself will be better understood by reference to the following description of an embodiment of the invention taken in conjunction with the accompanying drawings, wherein:

FIGS. 4A and 4B are radiographic photo images showing superimposed and actual sponges, respectively.

Figure 1:
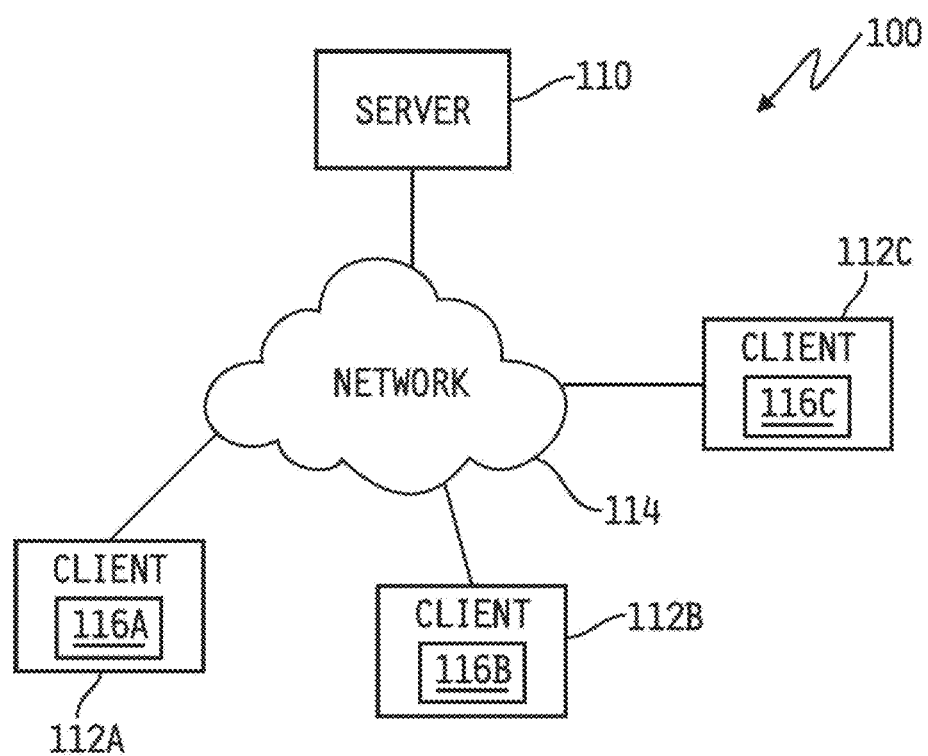
FIG. 1 is a schematic diagrammatic view of a network system in which embodiments of the present invention may be utilized.

Corresponding reference characters indicate corresponding parts throughout the several views. Although the drawings represent embodiments of the present invention, the drawings are not necessarily to scale and certain features may be exaggerated in order to better illustrate and explain the present invention. The flow charts and screen shots are also representative in nature, and actual embodiments of the invention may include further features or steps not shown in the drawings. The exemplification set out herein illustrates an embodiment of the invention, in one form, and such exemplifications are not to be construed as limiting the scope of the invention in any manner.

DESCRIPTION OF EMBODIMENTS OF THE PRESENT INVENTION

The embodiment disclosed below is not intended to be exhaustive or limit the invention to the precise form disclosed in the following detailed description. Rather, the embodiment is chosen and described so that others skilled in the art may utilize its teachings.

The detailed descriptions which follow are presented in part in terms of algorithms and symbolic representations of operations on data bits within a computer memory representing alphanumeric characters or other information. A computer generally includes a processor for executing instructions and memory for storing instructions and data. When a general purpose computer has a series of machine encoded instructions stored in its memory, the computer operating on such encoded instructions may become a specific type of machine, namely a computer particularly configured to perform the operations embodied by the series of instructions. Some of the instructions may be adapted to produce signals that control operation of other machines and thus may operate through those control signals to transform materials far removed from the computer itself. These descriptions and representations are the means used by those skilled in the art of data processing arts to most effectively convey the substance of their work to others skilled in the art.

An algorithm is here, and generally, conceived to be a self-consistent sequence of steps leading to a desired result. These steps are those requiring physical manipulations of physical quantities. Usually, though not necessarily, these quantities take the form of electrical or magnetic pulses or signals capable of being stored, transferred, transformed, combined, compared, and otherwise manipulated. It proves convenient at times, principally for reasons of common usage, to refer to these signals as bits, values, symbols, characters, display data, terms, numbers, or the like as a reference to the physical items or manifestations in which such signals are embodied or expressed. It should be borne in mind, however, that all of these and similar terms are to be associated with the appropriate physical quantities and are merely used here as convenient labels applied to these quantities.

Some algorithms may use data structures for both inputting information and producing the desired result. Data structures greatly facilitate data management by data processing systems, and are not accessible except through sophisticated software systems. Data structures are not the information content of a memory, rather they represent specific electronic structural elements which impart or manifest a physical organization on the information stored in memory. More than mere abstraction, the data structures are specific electrical or magnetic structural elements in memory which simultaneously represent complex data accurately, often data modeling physical characteristics of related items, and provide increased efficiency in computer operation.

Further, the manipulations performed are often referred to in terms, such as comparing or adding, commonly associated with mental operations performed by a human operator. No such capability of a human operator is necessary, or desirable in most cases, in any of the operations described herein which form part of embodiments of the present invention; the operations are machine operations. Useful machines for performing the operations of embodiments of the present invention include general purpose digital computers or other similar devices. In all cases the distinction between the method operations in operating a computer and the method of computation itself should be recognized. The various embodiments of present invention relate to methods and apparatus for operating a computer in processing electrical or other (e.g., mechanical, chemical) physical signals to generate other desired physical manifestations or signals. The computer operates on software modules, which are collections of signals stored on a media that represents a series of machine instructions that enable the computer processor to perform the machine instructions that implement the algorithmic steps. Such machine instructions may be the actual computer code the processor interprets to implement the instructions, or alternatively may be a higher level coding of the instructions that is interpreted to obtain the actual computer code. The software module may also include a hardware component, wherein some aspects of the algorithm are performed by the circuitry itself rather as a result of an instruction.

Some embodiments of the present invention also relate to an apparatus for performing these operations. This apparatus may be specifically constructed for the required purposes or it may comprise a general purpose computer as selectively activated or reconfigured by a computer program stored in the computer. The algorithms presented herein are not inherently related to any particular computer or other apparatus unless explicitly indicated as requiring particular hardware. In some cases, the computer programs may communicate or relate to other programs or equipments through signals configured to particular protocols which may or may not require specific hardware or programming to interact. In particular, various general purpose machines may be used with programs written in accordance with the teachings herein, or it may prove more convenient to construct more specialized apparatus to perform the required method steps. The required structure for a variety of these machines will appear from the description below.

Embodiments of the present invention may deal with "object-oriented" software, and particularly with an "object-oriented" operating system. The "object-oriented" software is organized into "objects", each comprising a block of computer instructions describing various procedures ("methods") to be performed in response to "messages" sent to the object or "events" which occur with the object. Such operations include, for example, the manipulation of variables, the activation of an object by an external event, and the transmission of one or more messages to other objects.

Messages are sent and received between objects having certain functions and knowledge to carry out processes. Messages are generated in response to user instructions, for example, by a user activating an icon with a "mouse" pointer generating an event. Also, messages may be generated by an object in response to the receipt of a message. When one of the objects receives a message, the object carries out an operation (a message procedure) corresponding to the message and, if necessary, returns a result of the operation. Each object has a region where internal states (instance variables) of the object itself are stored and where the other objects are not allowed to access. One feature of the object-oriented system is inheritance. For example, an object for drawing a "circle" on a display may inherit functions and knowledge from another object for drawing a "shape" on a display.

A programmer "programs" in an object-oriented programming language by writing individual blocks of code each of which creates an object by defining its methods. A collection of such objects adapted to communicate with one another by means of messages comprises an object-oriented program. Object-oriented computer programming facilitates the modeling of interactive systems in that each component of the system can be modeled with an object, the behavior of each component being simulated by the methods of its corresponding object, and the interactions between components being simulated by messages transmitted between objects.

An operator may stimulate a collection of interrelated objects comprising an object-oriented program by sending a message to one of the objects. The receipt of the message may cause the object to respond by carrying out predetermined functions which may include sending additional messages to one or more other objects. The other objects may in turn carry out additional functions in response to the messages they receive, including sending still more messages. In this manner, sequences of message and response may continue indefinitely or may come to an end when all messages have been responded to and no new messages are being sent. When modeling systems utilizing an object-oriented language, a programmer need only think in terms of how each component of a modeled system responds to a stimulus and not in terms of the sequence of operations to be performed in response to some stimulus. Such sequence of operations naturally flows out of the interactions between the objects in response to the stimulus and need not be preordained by the programmer.

Although object-oriented programming makes simulation of systems of interrelated components more intuitive, the operation of an object-oriented program is often difficult to understand because the sequence of operations carried out by an object-oriented program is usually not immediately apparent from a software listing as in the case for sequentially organized programs. Nor is it easy to determine how an object-oriented program works through observation of the readily apparent manifestations of its operation. Most of the operations carried out by a computer in response to a program are "invisible" to an observer since only a relatively few steps in a program typically produce an observable computer output.

In the following description, several terms which are used frequently have specialized meanings in the present context. The term "object" relates to a set of computer instructions and associated data which can be activated directly or indirectly by the user. The terms "windowing environment", "running in windows", and "object oriented operating system" are used to denote a computer user interface in which information is manipulated and displayed on a video display such as within bounded regions on a raster scanned video display. The terms "network", "local area network", "LAN", "wide area network", or "WAN" mean two or more computers which are connected in such a manner that messages may be transmitted between the computers. In such computer networks, typically one or more computers operate as a "server", a computer with large storage devices such as hard disk drives and communication hardware to operate peripheral devices such as printers or modems. Other computers, termed "workstations", provide a user interface so that users of computer networks can access the network resources, such as shared data files, common peripheral devices, and inter-workstation communication. Users activate computer programs or network resources to create "processes" which include both the general operation of the computer program along with specific operating characteristics determined by input variables and its environment. Similar to a process is an agent (sometimes called an intelligent agent), which is a process that gathers information or performs some other service without user intervention and on some regular schedule. Typically, an agent, using parameters typically provided by the user, searches locations either on the host machine or at some other point on a network, gathers the information relevant to the purpose of the agent, and presents it to the user on a periodic basis. A "module" refers to a portion of a computer system and/or software program that carries out one or more specific functions and may be used alone or combined with other modules of the same system or program.

The term "desktop" means a specific user interface which presents a menu or display of objects with associated settings for the user associated with the desktop. When the desktop accesses a network resource, which typically requires an application program to execute on the remote server, the desktop calls an Application Program Interface, or "API", to allow the user to provide commands to the network resource and observe any output. The term "Browser" refers to a program which is not necessarily apparent to the user, but which is responsible for transmitting messages between the desktop and the network server and for displaying and interacting with the network user. Browsers are designed to utilize a communications protocol for transmission of text and graphic information over a world wide network of computers, namely the "World Wide Web" or simply the "Web". Examples of Browsers compatible with embodiments of the present invention include the Chrome browser program developed by Google Inc. of Mountain View, Calif. (Chrome is a trademark of Google Inc.), the Safari browser program developed by Apple Inc. of Cupertino, Calif. (Safari is a registered trademark of Apple Inc.), Internet Explorer program developed by Microsoft Corporation (Internet Explorer is a trademark of Microsoft Corporation), the Opera browser program created by Opera Software ASA, or the Firefox browser program distributed by the Mozilla Foundation (Firefox is a registered trademark of the Mozilla Foundation). Although the following description details such operations in terms of a graphic user interface of a Browser, embodiments of the present invention may be practiced with text based interfaces, or even with voice or visually activated interfaces, that have many of the functions of a graphic based Browser.

Browsers display information which is formatted in a Standard Generalized Markup Language ("SGML") or a HyperText Markup Language ("HTML"), both being scripting languages which embed non-visual codes in a text document through the use of special ASCII text codes. Files in these formats may be easily transmitted across computer networks, including global information networks like the Internet, and allow the Browsers to display text, images, and play audio and video recordings. The Web utilizes these data file formats to conjunction with its communication protocol to transmit such information between servers and workstations. Browsers may also be programmed to display information provided in an eXtensible Markup Language ("XML") file, with XML files being capable of use with several Document Type Definitions ("DTD") and thus more general in nature than SGML or HTML. The XML file may be analogized to an object, as the data and the stylesheet formatting are separately contained (formatting may be thought of as methods of displaying information, thus an XML file has data and an associated method).

Similarly, JavaScript Object Notation (JSON) may be used to convert between data file formats.

The terms "personal digital assistant" or "PDA", as defined above, means any handheld, mobile device that combines computing, telephone, fax, e-mail and networking features. The terms "wireless wide area network" or "WWAN" mean a wireless network that serves as the medium for the transmission of data between a handheld device and a computer. The term "synchronization" means the exchanging of information between a first device, e.g. a handheld device, and a second device, e.g. a desktop computer, either via wires or wirelessly. Synchronization ensures that the data on both devices are identical (at least at the time of synchronization).

In wireless wide area networks, communication primarily occurs through the transmission of radio signals over analog, digital cellular or personal communications service ("PCS") networks. Signals may also be transmitted through microwaves and other electromagnetic waves. At the present time, most wireless data communication takes place across cellular systems using second generation technology such as code-division multiple access ("CDMA"), time division multiple access ("TDMA"), the Global System for Mobile Communications ("GSM"), Third Generation (wideband or "3G"), Fourth Generation (broadband or "4G"), personal digital cellular ("PDC"), or through packet-data technology over analog systems such as cellular digital packet data ("CDPD") used on the Advance Mobile Phone Service ("AMPS").

The terms "wireless application protocol" or "WAP" mean a universal specification to facilitate the delivery and presentation of web-based data on handheld and mobile devices with small user interfaces. "Mobile Software" refers to the software operating system which allows for application programs to be implemented on a mobile device such as a mobile telephone or PDA. Examples of Mobile Software are Java and Java ME (Java and JavaME are trademarks of Sun Microsystems, Inc. of Santa Clara, Calif.), BREW (BREW is a registered trademark of Qualcomm Incorporated of San Diego, Calif.), Windows Mobile (Windows is a registered trademark of Microsoft Corporation of Redmond, Wash.), Palm OS (Palm is a registered trademark of Palm, Inc. of Sunnyvale, Calif.), Symbian OS (Symbian is a registered trademark of Symbian Software Limited Corporation of London, United Kingdom), ANDROID OS (ANDROID is a registered trademark of Google, Inc. of Mountain View, Calif.), and iPhone OS (iPhone is a registered trademark of Apple, Inc. of Cupertino, Calif.), and Windows Phone 7. "Mobile Apps" refers to software programs written for execution with Mobile Software.

"PACS" refers to Picture Archiving and Communication System (PACS) involving medical imaging technology for storage of, and convenient access to, images from multiple source machine types. Electronic images and reports are transmitted digitally via PACS; this eliminates the need to manually file, retrieve, or transport film jackets. The universal format for PACS image storage and transfer is DICOM (Digital Imaging and Communications in Medicine). Non-image data, such as scanned documents, may be incorporated using consumer industry standard formats like PDF (Portable Document Format), once encapsulated in DICOM. A PACS typically consists of four major components: imaging modalities such as X-ray computed tomography (CT) and magnetic resonance imaging (MRI) (although other modalities such as ultrasound (US), positron emission tomography (PET), endoscopy (ES), mammograms (MG), Digital radiography (DR), computed radiography (CR), etc. may be included), a secured network for the transmission of patient information, workstations and mobile devices for interpreting and reviewing images, and archives for the storage and retrieval of images and reports. When used in a more generic sense, PACS may refer to any image storage and retrieval system.

FIG. 1 is a high-level block diagram of a computing environment 100 according to one embodiment. FIG. 1 illustrates server 110 and three clients 112 connected by network 114. Only three clients 112 are shown in FIG. 1 in order to simplify and clarify the description. Embodiments of the computing environment 100 may have thousands or millions of clients 112 connected to network 114, for example the Internet. Users (not shown) may operate software 116 on one of clients 112 to both send and receive messages network 114 via server 110 and its associated communications equipment and software (not shown).

Figure 2:
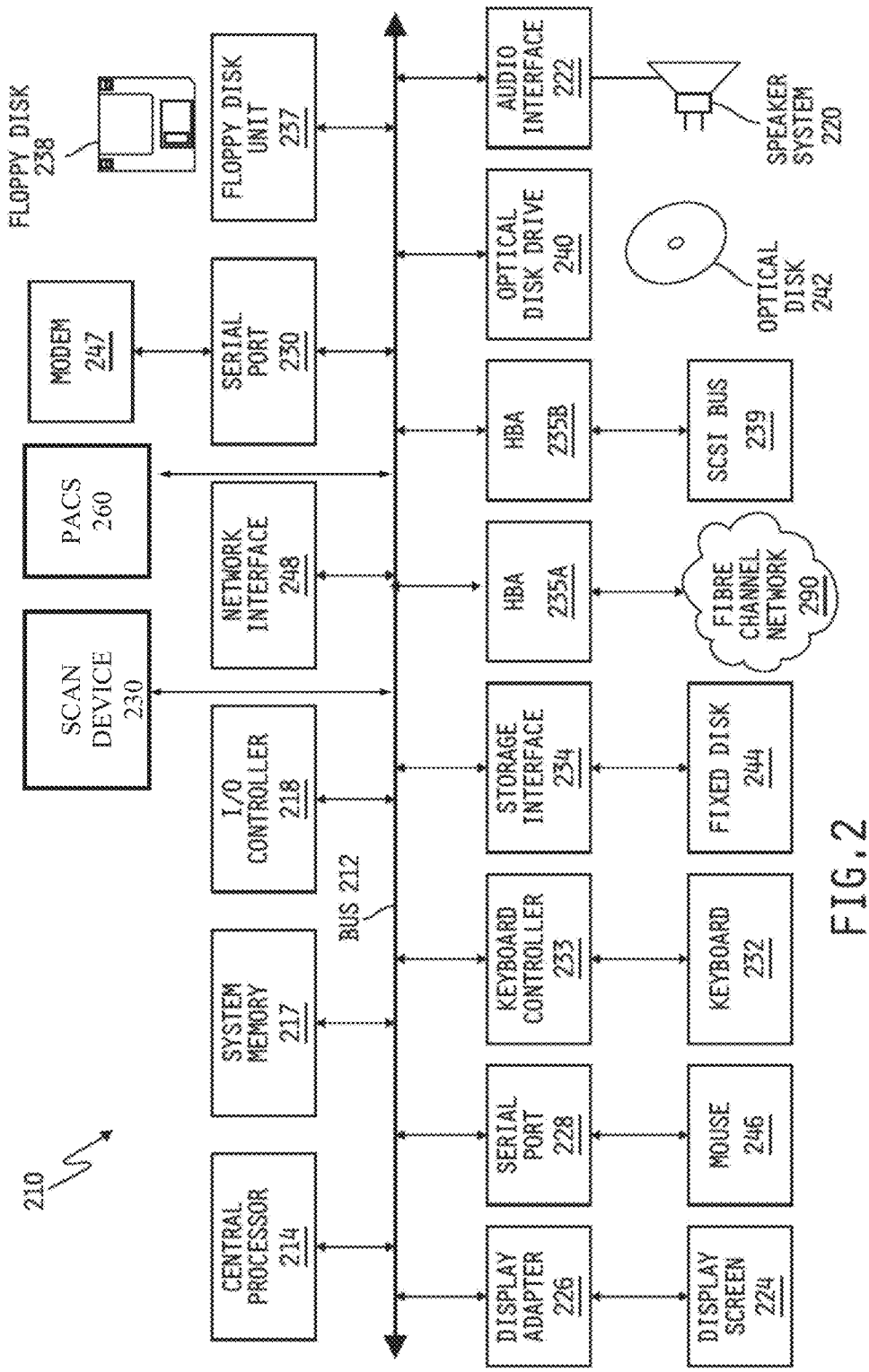
FIG. 2 is a block diagram of a computing system (either a server or client, or both, as appropriate), with optional input devices (e.g., keyboard, mouse, touch screen, etc.) and output devices, hardware, network connections, one or more processors, and memory/storage for data and modules, etc. which may be utilized in conjunction with embodiments of the present invention.

FIG. 2 depicts a block diagram of computer system 210 suitable for implementing server 110 or client 112. Computer system 210 includes bus 212 which interconnects major subsystems of computer system 210, such as central processor 214, system memory 217 (typically RAM, but which may also include ROM, flash RAM, or the like), input/output controller 218, external audio device, such as speaker system 220 via audio output interface 222, external device, such as display screen 224 via display adapter 226, serial ports 228 and 230, keyboard 232 (interfaced with keyboard controller 233), storage interface 234, disk drive 237 operative to receive floppy disk 238, host bus adapter (HBA) interface card 235A operative to connect with Fibre Channel network 290, host bus adapter (HBA) interface card 235B operative to connect to SCSI bus 239, and optical disk drive 240 operative to receive optical disk 242. Also included are mouse 246 (or other point-and-click device, coupled to bus 212 via serial port 228), modem 247 (coupled to bus 212 via serial port 230), and network interface 248 (coupled directly to bus 212).

Bus 212 allows data communication between central processor 214 and system memory 217, which may include read-only memory (ROM) or flash memory (neither shown), and random access memory (RAM) (not shown), as previously noted. RAM is generally the main memory into which operating system and application programs are loaded. ROM or flash memory may contain, among other software code, Basic Input-Output system (BIOS) which controls basic hardware operation such as interaction with peripheral components. Applications resident with computer system 210 are generally stored on and accessed via computer readable media, such as hard disk drives (e.g., fixed disk 244), optical drives (e.g., optical drive 240), floppy disk unit 237, or other storage medium. Additionally, applications may be in the form of electronic signals modulated in accordance with the application and data communication technology when accessed via network modem 247 or interface 248 or other telecommunications equipment (not shown).

Storage interface 234, as with other storage interfaces of computer system 210, may connect to standard computer readable media for storage and/or retrieval of information, such as fixed disk drive 244. Fixed disk drive 244 may be part of computer system 210 or may be separate and accessed through other interface systems. Modem 247 may provide direct connection to remote servers via telephone link or the Internet via an internet service provider (ISP) (not shown). Network interface 248 may provide direct connection to remote servers via direct network link to the Internet via a POP (point of presence). Network interface 248 may provide such connection using wireless techniques, including digital cellular telephone connection, Cellular Digital Packet Data (CDPD) connection, digital satellite data connection or the like. For example, while scan device 230 (e.g., an x-ray machine, ultrasound, etc.) and/or PACS 260 may be directly connected to bus 212, alternatively such systems may be accessed through network interface 248.

Many other devices or subsystems (not shown) may be connected in a similar manner (e.g., document scanners, digital cameras and so on). Conversely, all of the devices shown in FIG. 2 need not be present to practice the present disclosure. Devices and subsystems may be interconnected in different ways from that shown in FIG. 2. Operation of a computer system such as that shown in FIG. 2 is readily known in the art and is not discussed in detail in this application. Software source and/or object codes to implement the present disclosure may be stored in computer-readable storage media such as one or more of system memory 217, fixed disk 244, optical disk 242, or floppy disk 238. The operating system provided on computer system 210 may be a variety or version of either MS-DOS® (MS-DOS is a registered trademark of Microsoft Corporation of Redmond, Wash.), WINDOWS® (WINDOWS is a registered trademark of Microsoft Corporation of Redmond, Wash.), OS/2® (OS/2 is a registered trademark of International Business Machines Corporation of Armonk, N.Y.), UNIX® (UNIX is a registered trademark of X/Open Company Limited of Reading, United Kingdom), Linux® (Linux is a registered trademark of Linus Torvalds of Portland, Oreg.), or other known or developed operating system. In some embodiments, computer system 210 may take the form of a tablet computer, typically in the form of a large display screen operated by touching the screen. In tablet computer alternative embodiments, the operating system may be iOS® (iOS is a registered trademark of Cisco Systems, Inc. of San Jose, Calif., used under license by Apple Corporation of Cupertino, Calif.), Android® (Android is a trademark of Google Inc. of Mountain View, Calif.), Blackberry® Tablet OS (Blackberry is a registered trademark of Research In Motion of Waterloo, Ontario, Canada), webOS (webOS is a trademark of Hewlett-Packard Development Company, L.P. of Texas), and/or other suitable tablet operating systems.

Moreover, regarding the signals described herein, those skilled in the art recognize that a signal may be directly transmitted from a first block to a second block, or a signal may be modified (e.g., amplified, attenuated, delayed, latched, buffered, inverted, filtered, or otherwise modified) between blocks. Although the signals of the above described embodiments are characterized as transmitted from one block to the next, other embodiments of the present disclosure may include modified signals in place of such directly transmitted signals as long as the informational and/or functional aspect of the signal is transmitted between blocks. To some extent, a signal input at a second block may be conceptualized as a second signal derived from a first signal output from a first block due to physical limitations of the circuitry involved (e.g., there will inevitably be some attenuation and delay). Therefore, as used herein, a second signal derived from a first signal includes the first signal or any modifications to the first signal, whether due to circuit limitations or due to passage through other circuit elements which do not change the informational and/or final functional aspect of the first signal.

Figure 3:
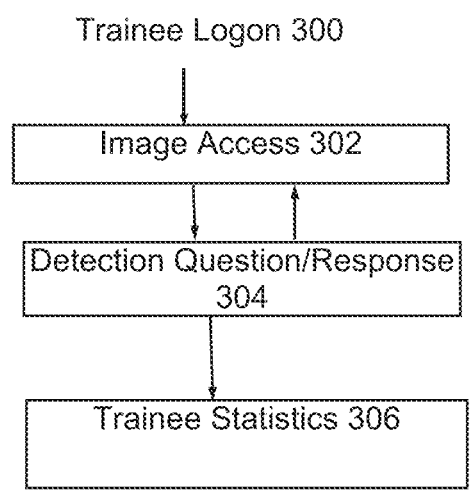
FIG. 3 is a flow chart diagram of the operation of the present invention relating to physician training.

FIG. 3 shows a flow chart of an illustrative training exercise. In step 300, a trainee (e.g., a physician desiring further RFO image detection practice) logs onto the system, and in step 302 the trainee accesses an image that may or may not have an RFO. In step 304, the system provides feedback, for example confirming a detection of an RFO, confirming the absence of an RFO, notifying the trainee of a missed RFO, and notifying the trainee that she/he had misidentified the image as having an FRO. The trainee may loop back to step 302 for a certain number of images or alternatively for a certain amount of time, and eventually proceed to step 306 where the trainee statistics for the current session, and optionally for other sessions, are displayed for the trainee. For example, the steps of the flow chart of FIG. 3 may be implemented on the arrangement of FIG. 1.

FIG. 4A shows an image of a synthetic RFO, while FIG. 4B shows an image of an actual RFO.

Figure 5A:
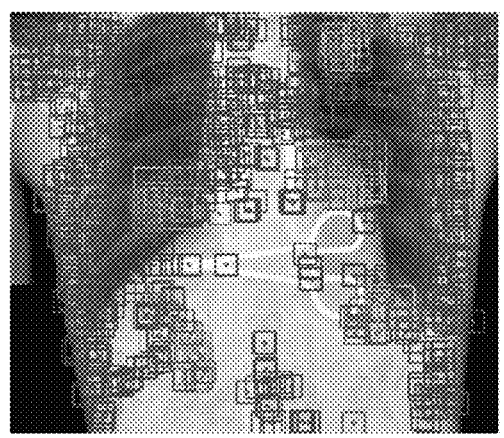
FIGS. 5A and 5B are radiographic photo images showing intermediate and final detection areas according to one embodiment of the present invention.
Figure 5B:
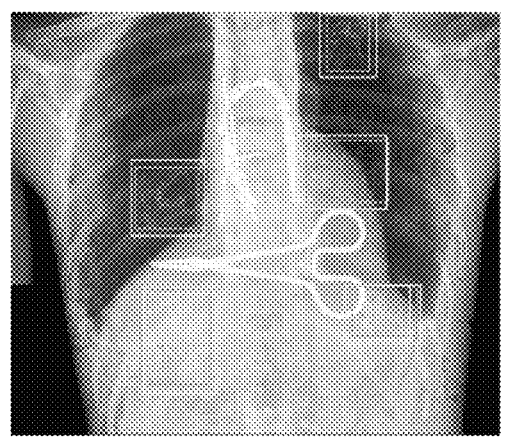

FIG. 5A shows an image with multiple potential locations for detection of an object. FIG. 5B shows an image with final determined selected areas where items were identified.

In developing suitable images for training physicians, embodiments of the present invention utilize synthesizing images with objects of interest based on actual images. In this way we can synthesize a large number of images under varying conditions and have these automatically annotated for the correct location and identification. The basic idea is to paste into an actual scan image an actual scan image of the object of interest. The implantation in conducted such that the implanted object is indistinguishable from an actual one. The algorithm steps include one or more of the steps as follows:

1. Compute the contrast difference between Retained Surgical Implements (RSIs) and their neighborhood using actual RSI scan images. This is used to set the mean and standard deviation of the normal distribution of the implanted objects intensity contrast.

2. Capture actual scan images of foreign objects of interest with good contrast.

3. Segment the actual scan images of foreign objects to form a binary mask M1. That is, the mask M1 is composed of the set of pixels belonging to the object. To do the segmentation, manually mark a rectangular region where the object of interest is and apply an adaptive thresholding algorithm.

4. Detect uniform background regions and exclude them from being candidates for implantation. Candidate location should be located within the imaged body area.

5. Randomly select a desired position (P), rotation (R), scale (S), thickness (T), and intensity contrast (C) of the superimposed object. The parameters are selected using a Gaussian probability distribution except for (P) which is distributed according to a uniform distribution. Reject positions (P) that are in the included in uniform background regions.

6. Adjust the resolution of the implanted object to match that of the target image so that in both images a set number of pixels corresponds to the same physical size.

7. Adjust the intensity of the implanted object by dividing its intensity values by its average intensity (in the area covered by the mask M2) and multiplying the intensity values by the desired intensity contrast parameter (C).

8. Adjust the thickness of the implanted object using the generated thickness parameter (T) thus making strokes in it thinner or thicker. The thickness adjustment is done using the distance transform.

9. Transform and warp the masks M1 and the foreign object image according to the random rotation (R) and scale (S) parameters.

10. Smooth the mask M1 using a Gaussian smoothing filter to produce a mask M2 so that the transition between object and no object is smooth. After the smoothing M2 has values between 0 and 1.

11. Multiply the implanted foreign object image by M2 and add the result to the target image at location (P). This is the actual implantation. It follows the physics of X-ray image generation where intensities are combined by addition instead of replacement as is the case in ordinary images.

12. Dilate the mask M1 to produce a wider mask M3. Smooth the implanted image using a Gaussian filter but only at locations belonging to M3.

13. Produce a binary mask M4 in which 1 indicates that the corresponding location in M3 is greater than 0, and 0 indicates that the corresponding location in M3 is 0. M4 is the mask of the known implanted object location and is used for verification purposes.

The annotation of the synthesized images is done by finding axis aligned bounding boxes for the imported objects.

These boxes are positive boxes (P). In addition to the positive boxes there is a need to find negative boxes (N). The need for the negative boxes will be explained later. Negative boxes are identified at candidate locations where change occurs and which have characteristics which are similar to object characteristics. Negative candidate locations may not overlap with each other and may not overlap with the positive candidate locations. In our current implementation typically there are approximately 22-40 negative candidate location in each image.

Next there is an algorithm and methods for assessing the level of difficulty in each image whereas the level of difficulty is being updated continuously based on user performance. In this manner is possible to order the images from easy to hard and train the observer in a gradual manner.

The level of difficulty for achieving the identification of RSIs is affected by three main factors, the type of the object and its size, the contrast of the implanted object, and the clutter in the image that can distract the observer and hide the object. The three main factors are handled as follows:

1. Type of object and its size—we divide the set of objects of interest into subsets were each subset contains objects of similar characteristics and difficulty level. For example, one subset may contain sponges, a second subset may contain small needles, and a third subset may contain large needles. We maintain a separate level for each object class. As the training progresses, the user advances concurrently in the different object class categories. The training is complete once the user has achieved the highest level in all classes.

2. Contrast—The contrast parameter is continuous. A contrast of zero means that the object is indistinguishable from its surroundings in terms of intensity. As the contrast increases the object becomes more and more distinguishable with respect to its neighborhood. Thus, the difficulty level can be controlled by decreasing the contrast.

3. Clutter—we consider images as having high visual clutter levels if there is high variation of intensity within them. Images with high visual clutter make it more difficult to identify objects in them. When the contrast of an object is identical to the standard deviation of intensity in the image it hard to distinguish this object. Thus, to control the difficulty of recognizing an object in an image we increase the difficulty level for images with high intensity standard deviation. We compute a baseline standard deviation for images and then increase the difficulty level for images with higher standard deviation. The increase in standard deviation is quantized (e.g. into chunks of 10) and the level of difficulty of an image is raised by the number of chunks. Examples of low and high clutter images are shown in FIGS. 1 and 2 respectively.

Figure 6A:
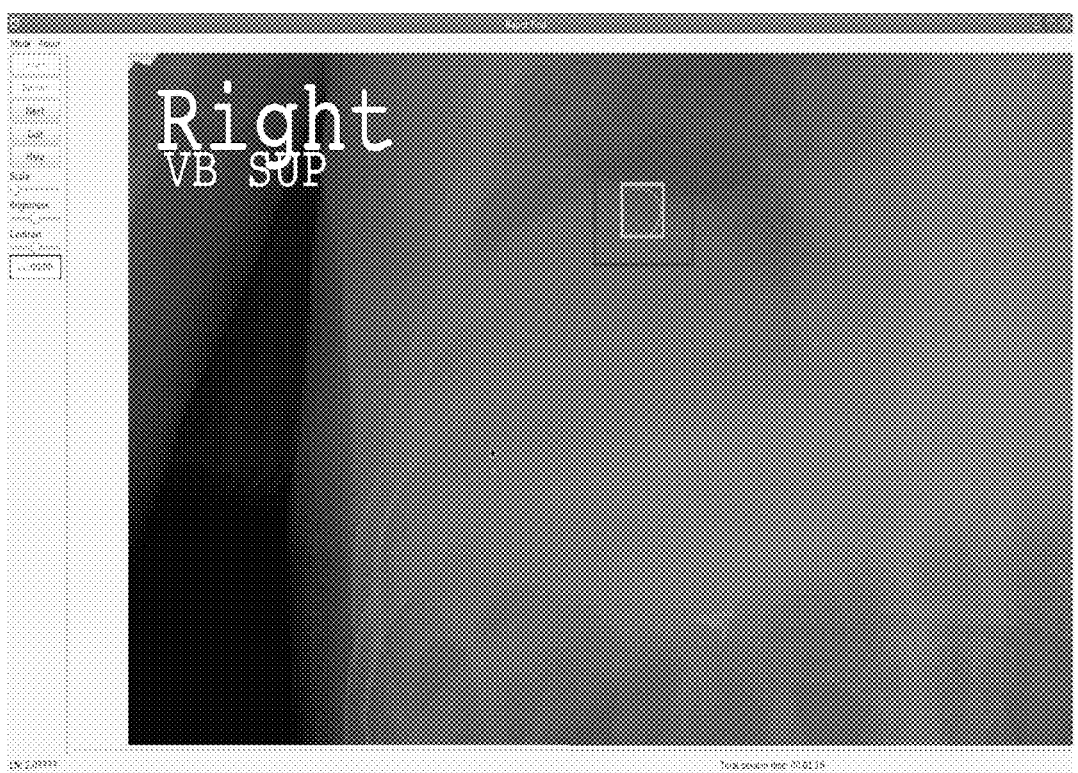
FIGS. 6A and 6B are radiographic photo images showing areas of potential retained objects according to one embodiment of the present invention.
Figure 6B:

FIG. 6A provides an example of an image with low visual clutter where needle identification is easy, whereas FIG. 6B provides an example of an image with high visual clutter where needle identification is difficult. For training sets of images initially a large set of thousands of images are generated in a set number (e.g. 10) of levels of difficulty. The images in each level contain all the possible objects of interest (e.g. sponges, small needles, and large needles) for this particular level of difficulty. As explained above generating an image with a given difficulty level depends on the contrast parameter for this level. Thereafter the levels are adjusted based on the intensity variance in the image.

The initial difficulty assignment is an estimate that is based on some prior beliefs. There are, however, other factors that may affect the difficulty. To address this, we dynamically update the difficulty level of each image based on user performance. Images with correctly identified objects have their difficulty level reduced whereas images with incorrectly identified objects have their level of difficulty increased. The precise process for updating the level of difficulty is described below.

Figure 7:
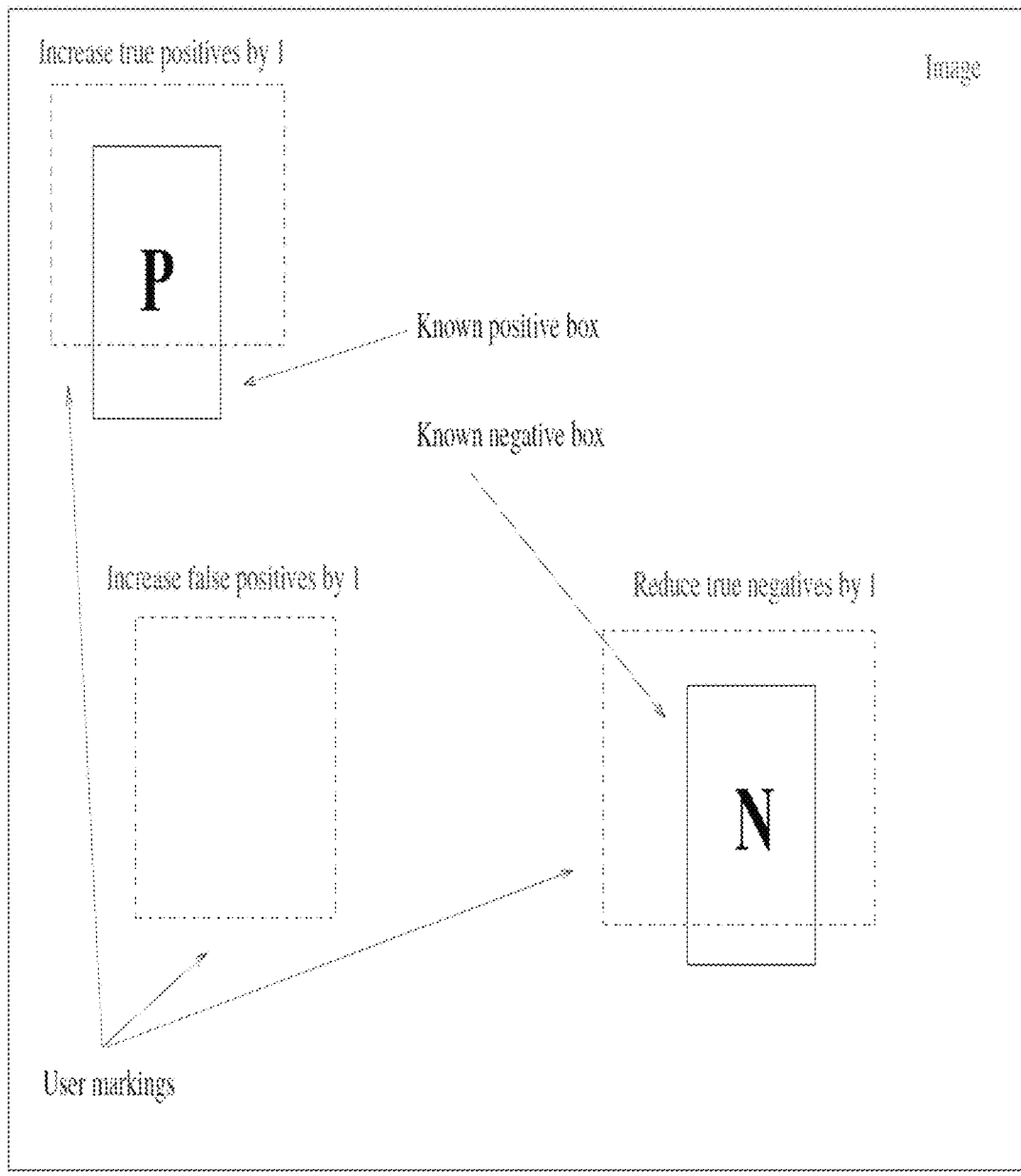
FIG. 7 is a schematic diagram of a user evaluation system and method of one embodiment of the present invention.

The level of performance of an observer may be assessed by an algorithm and methods. In this way it is possible to determine when the observer mastered an existing level and can move to the next level so that the training remains challenging and effective. Objects of interest are identified by the observer by marking rectangles around them. The observer's rectangles are then compared to the true (known) object bounding boxes. Consider FIG. 7, representing a positive box P where an object is known to reside and a known negative box N where an object is known not to reside. User markings are shown dashed lines. Some user markings overlap with the positive box, some overlap with the negative box, and some not overlap the any boxes.

The issue here is that while there are two classes, one of positive and one of negative boxes, the user only marks positive boxes. This allows us to compute a true positive (TP) rate and false positive (FP) rate by checking if a user marked a box that overlaps with a positive box or not, respectively. Since the user does not mark negative boxes, it is not possible for us to determine a false negative (FN) rate. The true negative (TN) rate, on the other hand, may be computed by counting the number of negative boxes that are not covered by any user selection.

Given a user marked box and an existing box (positive or negative), we determine that the user box matches the known box if area of the intersection between the two boxes is greater or equal to 25% of the area of either the known box or user box. Each image is assigned four counters: a true positive counter which is initialized to zero, a false positive counter which is initialized to zero, a true negative counter which is initialized to the total number of negative boxes in the image, and a false negative counter which is initialized to zero. If a user box matches a known positive box, the true positive counter for this image is increased by one. If a user box matches a known negative box, the true negative counter for this image is decreased by one. If a user box does not match any known positive or negative boxes, the false positive counter for the image is increased by one. The true negative counter is never updated.

The user accuracy is defined by the sum of the true positive and true negative counts divided by the sum of the true positive, true negative, false positive, and false negative counts. A user with perfect performance will have an accuracy of one whereas a user with completely incorrect markings will have an accuracy of zero. The true negative boxes and negative counts are necessary to guard against a labeling which uses one big box for the entire image. A user box, which encompasses the entire image will result in a high true positive rate, low true negative rate, and overall low accuracy.

The level of difficulty may be updated using an algorithm and methods based on her/his performance. In this way the user starts at the lowest level of difficulty and progresses to more challenging levels after successfully completing prior levels. In addition, while the user is labeling images, the difficulty level of the images themselves also change based on the performance of the user. An image which is successfully completed by a user assists the user in moving to the next level of difficulty and at the same time has its level reduced. By changing the difficulty level of the image we can adapt the initial level of difficulty originally set by our algorithm to actual levels of difficulty experienced by users.

In the training and testing all the possible kinds of objects are mixed for which the user should be trained inside the images. This is so that the training is more realistic and so that the user does not know for which item to look for as is the case in real life. Further, we include images that do not have any relevant objects in them so as to make the conditions resemble real-life cases were most images do not contain RSI objects in them. The algorithm for changing the user's level and image difficulty level is as follows:

1. Each user has several independent difficulty levels, one for each object type. For example, a user may have a difficulty level for sponges, a difficulty level for small needles, and difficulty level for large needles. The initial user difficulty levels are set to one. The maximal difficulty level achievable is 10. The initial image difficulty level is set by our algorithm to a number between 1 and 10 whereas 1 indicates easy and 10 indicates difficult.

2. When a user successfully does not mark anything in an image without objects, there are no changes to the user's level or image difficulty level. This is because no object was identified.

3. When a user incorrectly identifies objects on an image that does not have ones in it, the user's level needs to be decreased. Since in our system the user need not classify marked objects, it is not clear what was the intention of the user by marking the object. Thus, to decide on the precise item for which the difficulty level should be reduced, we compare the area of the marked box to the average area of marked boxes in all categories for this particular user. We then select the item type with the area most similar to the one marked by the user and decrease the user's level for that item.

4. When a user marks boxes on images that contain objects we determine an update to the user's level as well as the image's difficulty level based on 3 factors: the accuracy of the labeling, the time it took the user to perform the labeling, and the number of operations the user performed while doing the labeling. The number of operations include the number of times the user zoomed in and out the image, change the contrast of the image, change the intensity of the image, translated the image, or marked and deleted boxes.

(a) The accuracy is computed using a recall metric as TP divided by (TP+FN) hereas TP and FN were defined in Section above. We then subtract the recall from one to get the error rate (ER) factor. The error rate factor is a number between 0 and 1 and we scale it to be between 0 and 2. The higher the error rate, the more difficult the image is deemed.

(b) The time factor (TF) is computed by the ratio between the time it took the user to label this image, and the average time it took other users to label this same image. If this is the first user to label this image, the average time for image is set to the user's time. The computed ratio is restricted to a set range (e.g., 0.1 . . . 5). The time factor is then normalized to a number between 0 and 2. The higher the time it takes to label the image, the more difficult the image is deemed.

(c) The number of operations factor (NF) is computed by the ratio between the number of operations it took the user to label this image, and the average number of operations it took other users to label this same image.

If this is the first user to label this image, the average number of operations for image is set to the user's average. The computed ratio is restricted to a set range (e.g., 0 . . . 5). The number of operations factor is then normalized to a number between 0 and 2. The higher the number of operations, the more difficult the image is deemed.

(d) Assuming that the number of consecutive successful image labeling necessary for user to move to the next level is N (e.g. N=5), the maximal level change induced by each image is −1=N. Using a weight of W1 for the accuracy factor, a weight of W2 for the time factor, and a weight of W3 for the number of operations, whereas W1+W2+W3=1 we take a weighted sum as follows to compute an update U which could be positive or negative:

$$U = ((ER-1) \cdot W1 + (TF-1) \cdot W2 + (NF-1) \cdot W3) \cdot \frac{1}{N}$$

(e) The value of U is then added to the user level for the appropriate object, and for the difficulty level of the image. Note that an object or image level is restricted to the range 1 . . . 10.

User performance data may be collected by an algorithm and methods which may then be used to improve user training, develop best practice guidelines, and to improve automated detection systems. This is an aspect of the invention. Current practices, where RSIs of actual cases are collected, result in extremely small test collections (e.g. 10 images) which do not offer much insight into the reasons and or situations where RSIs are missed. Such small test collections also does not offer much insight on effective ways to scan an image for RSIs and as a consequence there are no best practice recommendations in this area.

In the systems of embodiments of the present invention, all user actions are recorded and saved. These may then be analyzed and used to determine best practice guidelines. For example, it is possible to identify a set of difficult images where missed detection is common and analyze the practices of physicians who successfully detect RSIs in them. Likewise it is possible to identify successful and effective observers and compare them to unsuccessful or ones.

The analysis is based on database tables where all the information is stored and that can be viewed in different ways.

The system is also able to replay the user actions for any marked image and allow an analyst to observe them in the exact way they were conducted. For this purpose we collect all mouse and keyboard events together with time stamps. In addition to the recorded events we also compute several key metrics per user, image, and implanted object. The database contains the following tables and metrics that are computed based on them:

※ User table: personal information, user level, number of images completed, mean image accuracy, mean labeling time per image, mean number of operations per image)

※ Image table: image name and path, difficulty level, number of users training on it, mean user accuracy, mean labeling time, mean labeling operations number)

※ Object table: object information, number of users training on it, mean detection rate, mean scale/brightness/contrast when detecting it, mean object aspect ratio.

※ Image results table: user/image/object identifiers, TP, FP, FN, TN counts per image, time per image, operations per image.

※ Object results table: user/image/object identifiers, detection result, scale/brightness/contrast when detected, object aspect ratio.

※ User history table: user/image identifiers, user level per object type.

※ User markings table: user/image identifier, training/testing mode flag, upper left coordinates, width and height of bounding box.

The user performance data can be used to chart the progress of individuals and the mean progress. This may be used to assess the following:

※ The effectiveness of the training (the average improvement after training).

※ The user progression curve and consequently the time or case numbers necessary for training a user and after which performance increases are marginal.

※ Categorization of difficult cases.

※ Categorization of unsuccessful observers.

※ The correlation between user markings and automated algorithm markings.

※ Performance comparison between users and an automated labeling system to establish a baseline as to acceptable performance.

Note that currently there are no acceptable performance standards as to RSI detection and not much is known as to circumstances that affect performance. The training system we developed will help establish such standards by considering average performance and will help analyze circumstances that affect performance.

Training the observer may be accomplished by training physicians in recognizing RSIs in XR images. Currently, even experienced radiologists see in practice only a small number of images containing RSIs due to the low incidence of such images. Embodiments of the present invention provide systems for training physicians to detect RSIs.

In one embodiment, the system is a software service that provides synthesized images to observers, measure their performance, provides feedback as to their performance, adapt the difficulty level of the cases presented, and progress in a similar manner until a satisfactory progress level has been achieved. The software may be deployed using a software installation package or by launching a web service application in which the user runs client code through a standard web browser.

The client connects to a remote server which contains a database server and an image server.

Our system for RSI detection is intended to train physicians (e.g. resident physicians) and to increase their awareness to the problem of RSIs. We are not aware of any methodical training that is done. The invention seeks to train physicians so as to reduce the incidence of RSIs. When a physician is given an image to analyze, she/he does not know whether there are any objects in the image, what are the object types, how many object types there are, and how many objects there are. This is so as to make the training resemble a real scenario in the hospital. The physician may interact with the image by changing its contrast or intensity, zoom in or out, and translate the image. There are three main modes in the training software:

※ A training mode—where after marking objects the user is shown the true object locations (marked in a different color) so that she/he can learn from mistakes.

※ A testing mode—where after marking objects the user is not shown the true object locations.

※ An administrator mode—where the administrator may observe the performance of users, analyze user performance, and replay specific training sessions.

User levels are changed based on their performance in the current level as described in above. A user needs to complete a set number of consecutive correct labeling before proceeding to the next level. Thus, while the user's level is updated continuously, when using the user's level to retrieve a training image from the database, the level is truncated. The retrieved image is selected to match the user's truncated level. The parameters of our approach (e.g. the number of consecutive correct labeling a user must achieve before moving to the next level) are set by testing their effect on actual training sessions. A parameter is selected to maximize the training effectiveness while shortening the training duration.

Determining when a user has successfully mastered the detection of RSIs is not straightforward as there are no accepted standards as to the level of detection by a human observer. Some studies have shown that observers fail to detect needles when their size is small. Since are able to synthesize very difficult cases with small objects and/or poor contrast in which there is very little information, we need a stop criterion for the training session. The stop criterion is learned from user performance as follows:

※ The minimum number of training images is set to the smallest number that produces measurable gain in performance. We chart average performance vs. number of images and determine a point where additional images do not result in improved performance.

※ The maximal difficulty level should be such that a set percentage of observers must be able to detect objects in such images.

※ The attained user accuracy must be within a set fraction of standard deviation from the mean user performance.

※ The training must result in continuous performance improvement. When performance improvement stops the training ends.

※ We set a limit on the maximal number of images a user is required to label as a set fraction of standard deviation from the mean number of images completed by other users.

※ We set a limit on the maximal time a user is required to label as a set fraction of standard deviation from the mean time completed by other users.

The overall training session is performed as follows. The training starts with a test containing sufficiently difficult images. The purpose of the test is to determine the level at which the user starts the training and also to establish a baseline for measuring user improvement due to training. Thereafter the user must complete a training session as described above. As the training reaches to an end the user is given more and more images containing no objects to simulate actual images in which the objects are not normally present. At the end of the training session a final test is conducted to establish the improvement due to training. The images used in any of the tests or the training session do not repeat for a given user. That is, if an image was used in the initial test or the training it cannot appear in the final test. Note, however, that images used to train or test other users may appear in the training or testing another user. This is done so that we gain an accurate estimate as to the level of difficulty of the images included in the test.

The level of difficulty of images in the initial and final test is set to be the same so that improvement during to training may be measured.

To assess whether the training is effective in contributing to observer ability to detect RSIs we compare the performance of observers who went through training by our system and observers who did not. Note that in contrast to medication effectiveness testing where different patients must be used in the test and control groups, in the case of training the same observer may be used in both the test and control group where the performance in the control group is simply the performance before training and the performance in the test group is the performance after training.

Embodiments of the present invention are concerned with a training system for detection and classification of artificial objects in scan Images, including but not limited to x-ray images. While the description here focuses mainly on RSIs, this is intended as a use case. The invention is not limited to RSIs and applies in the same manner to a wide range of applications where training for recognition and identification in x-ray images is required. Such applications include, but are not limited to the following:

* Luggage screening
* Person screening
* Cargo screening
* Implantable medical device identification
* Retained surgical objects detection.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A server for training a user on detection of Retained Foreign Objects having radiographic markers adapted to change shape during surgery (RFOs) in images, said server comprising:
    an image database including a plurality of images of bodies, a first portion of the plurality of images having RFOs depicted, a second portion of the plurality of images lacking a depicted RFO;
    an interaction module for sending a sub-set of that plurality of images to a user device, the interaction module also adapted to receive user communication relating to the presence or absence of an RFO in a particular image; and
    a recording module for recording the correspondence between user communication received relating to each of the first portion and second portion of the images.

2. A method of using a computer to synthesize the presence of a Retained Foreign Object having radiographic markers adapted to change shape during surgery (RFO) in a body image, said method comprising the steps of:
    obtaining a first image of a body without any RFOs;
    obtaining a second image of a body having an RFO;
    extracting features of the RFO from the second image; and
    superimposing the extracted features with the first image to create said synthesized image.

3. A method of training human observers in visual detection of predetermined objects within areas of interest around a surgical field in a scan image, said method comprising the steps of:
    computing the contrast difference between areas of interest relating to the predetermined objects and their neighborhood using areas of interest in scan images;
    capturing scan images of foreign objects of interest with contrast with a known level of difficulty;
    segmenting the scan images of areas of interest to form a first binary mask; and
    transforming the first mask and the areas of interest in the image according to the random rotation (R) and scale (S) parameters; and
    smoothing the mask M1 using a Gaussian smoothing filter to produce a second binary mask so that the transition between areas of interest and other areas is smooth.

4. The method of claim 3 further including the step of detecting uniform background regions and exclude the uniform background regions from being candidates for implantation.

5. The method of claim 3 wherein the step of computing the contrast difference includes setting the mean and standard deviation of the normal distribution of the areas of interest intensity contrast.

6. The method of claim 3 wherein the step of segmenting includes having the first mask being composed of the set of pixels belonging to the area of interest.

7. The method of claim 6 wherein the segmentation involves marking a rectangular region where the areas of interest reside and applying an adaptive thresholding algorithm.

8. The method of claim 3 wherein the step of transforming includes randomly selecting a desired position (P), rotation (R), scale (S), thickness (T), and intensity contrast (C) of the area of interest.

9. The method of claim 8 wherein the step of transforming involves the parameters being selected using a Gaussian probability distribution except for (P) which is distributed according to a uniform distribution.

10. The method of claim 3 wherein the step of transforming includes adjusting the resolution of the area of interest to match that of the target image so that in both images a set number of pixels corresponds to the same physical size.

11. The method of claim 8 wherein the step of transforming includes adjusting the intensity of the area of interest by dividing its intensity values by its average intensity and multiplying the intensity values by the desired intensity contrast parameter (C).

12. The method of claim 11 wherein the step of adjusting the intensity involve the area covered by the second mask.

13. The method of claim 8 wherein the transformation step involves adjusting the thickness of the area of interest using the generated thickness parameter (T) to thereby make strokes in it thinner or thicker using the distance transform.

14. The method of claim 8 wherein the step of transforming involves warping the first mask and the area of interest according to the random rotation (R) and scale (S) parameters.

15. The method of claim 3 wherein the step of smoothing the first mask uses a Gaussian smoothing filter to produce a second mask so that the transition between object and no object is smooth and wherein after smoothing the second mask has a value of between 0 and 1.

16. The method of claim 3 further comprising the step of multiplying the area of interest by the second mask and add the result to the target image at location (P), thereby intensities are combined by addition instead of replacement.

17. The method of claim 3 further comprising the step of dilating the first mask to produce a wider third mask and smoothing the area of interest using a Gaussian filter but only at locations belonging to the third mask.

18. The method of claim 3 further comprising the step of producing a fourth binary mask in which 1 indicates that the corresponding location in the third mask is greater than 0, and 0 indicates that the corresponding location in the third mask is 0 or that the fourth mask is the mask of the known area of interest location so as to be used for verification purposes.

19. The method of claim 3 wherein after the smoothing step, the second binary mask has values between 0 and 1.

* * * * *